(12) United States Patent
Yamahira et al.

(10) Patent No.: US 9,638,516 B2
(45) Date of Patent: May 2, 2017

(54) OVEN WALL SHAPE MEASURING APPARATUS, OVEN WALL SHAPE MEASURING SYSTEM, AND OVEN WALL SHAPE MEASURING METHOD

(75) Inventors: Naoshi Yamahira, Tokyo (JP); Toshifumi Kodama, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 442 days.

(21) Appl. No.: 13/997,987

(22) PCT Filed: Dec. 19, 2011

(86) PCT No.: PCT/JP2011/079352
§ 371 (c)(1),
(2), (4) Date: Jun. 25, 2013

(87) PCT Pub. No.: WO2012/090758
PCT Pub. Date: Jul. 5, 2012

(65) Prior Publication Data
US 2013/0286406 A1    Oct. 31, 2013

(30) Foreign Application Priority Data

Dec. 27, 2010  (JP) ................................. 2010-291018
Dec. 16, 2011  (JP) ................................. 2011-275631

(51) Int. Cl.
*G01B 11/24*  (2006.01)
*F27D 21/00*  (2006.01)
(Continued)

(52) U.S. Cl.
CPC .............. *G01B 11/24* (2013.01); *C10B 45/00* (2013.01); *F27D 21/0021* (2013.01); *G01B 11/2518* (2013.01); *G01N 21/954* (2013.01)

(58) Field of Classification Search
CPC ........ G01N 2021/9063; G01N 21/9036; G01N 21/90; C10B 45/00; F27D 21/0021; G01B 11/24; G01B 11/25
(Continued)

(56) References Cited

U.S. PATENT DOCUMENTS 4,227,802 A    10/1980  Scholdstrom et al.
4,708,482 A *  11/1987  Neiheisel ................ C21C 5/441
                                                     250/214 B
(Continued)

FOREIGN PATENT DOCUMENTS

CN    1290969 C    12/2006
EP    0787970 A2    8/1997
(Continued)

OTHER PUBLICATIONS

201180062802.X mechanical translation of second office action.*
(Continued)

*Primary Examiner* — Tri T Ton
(74) *Attorney, Agent, or Firm* — Holtz, Holtz & Volek PC (57) ABSTRACT

An oven wall shape measuring apparatus includes: a slit laser light source that is arranged in a thermally-insulated protection box having a slit-like window and emits slit-like laser light; a laser light mirror that reflects the laser light and irradiates an oven wall surface with the laser light via the window; an imaging mirror that reflects reflected light due to irradiation of the laser light and self-emitting light emitted from the oven wall surface, the reflected light and the self-emitting light entering the thermally-insulated protection box via the window; and an imaging device that images, via an optical filter, the self-emitting light and the reflected light that are reflected from the imaging mirror.

10 Claims, 5 Drawing Sheets

(51) Int. Cl.
*C10B 45/00* (2006.01)
*G01N 21/954* (2006.01)
*G01B 11/25* (2006.01)

(58) Field of Classification Search
USPC .......... 356/601–613, 376, 241, 5, 384, 381;
382/141–149, 154, 100
See application file for complete search history.

(56) References Cited

U.S. PATENT DOCUMENTS

| | | | |
|---|---|---|---|
| 5,594,548 A * | 1/1997 | Kobayashi | F27D 21/02 356/241.1 |
| 5,715,328 A * | 2/1998 | Tsukihara | G01N 21/88 348/83 |
| 5,721,416 A * | 2/1998 | Burghardt | B23K 26/0738 219/121.73 |
| 7,355,768 B1 * | 4/2008 | Billmers | G02B 5/32 359/15 |
| 2008/0170238 A1 | 7/2008 | Ochi et al. | |

FOREIGN PATENT DOCUMENTS

| | | |
|---|---|---|
| EP | 1 473 350 A1 | 11/2004 |
| EP | 1473350 A1 | 11/2004 |
| EP | 1655570 A1 | 5/2006 |
| JP | 4-54208 Y2 | 12/1992 |
| JP | 07-91931 A | 4/1995 |
| JP | 2000-266475 A | 9/2000 |
| JP | 2004-077019 A | 3/2004 |
| JP | 2008175625 A | 7/2008 |
| JP | 2010133950 A | 6/2010 |

OTHER PUBLICATIONS

Chinese Office Action (and English translation thereof) dated Sep. 14, 2015, issued in counterpart Chinese Application No. 201180062802.X.

Chinese Office Action (and English translation thereof) dated Mar. 11, 2015, issued in counterpart Chinese Application No. 201180062802.X.

Japanese Office Action (and English translation thereof) dated Jul. 14, 2015, issued in counterpart Japanese Application No. 2011-275631.

Japanese Office Action (and English translation thereof) dated Feb. 9, 2016, issued in counterpart Japanese Application No. 2011-275631.

Extended European Search Report (EESR) dated Jan. 4, 2017 issued in European counterpart application No. 11852692.0.

* cited by examiner

OVEN WALL SHAPE MEASURING APPARATUS, OVEN WALL SHAPE MEASURING SYSTEM, AND OVEN WALL SHAPE MEASURING METHOD

Field

The present invention relates to an oven wall shape measuring apparatus, an oven wall shape measuring system, and an oven wall shape measuring method.

BACKGROUND

Examples of deposits on oven wall surfaces that affect lives of oven bodies of industrial ovens include carbon adhered on an oven wall surface of a coke oven. In a coke oven, operations of carbonizing coal introduced into the oven for a certain period of time and discharging the formed red-hot coke outside the coke oven by a coke extruding apparatus are repeated. When such operations are performed, carbon deposits on the oven wall surface of the coke oven and grows unevenly. If this growth proceeds, parts of the deposited carbon may be peeled off and fall in the oven.

Moreover, firebricks forming the oven wall surface are subjected to mechanical or thermal impacts upon the introduction of coal or gradually eroded by, for example, parts of the firebricks being peeled off along with the carbon grown on the wall surface. As a result, the oven wall surface of the coke oven becomes irregular, causing clogging in the oven during the coke extrusion operation. Clogging in the oven not only reduces operational efficiency of the coke oven but also places heavy load on the oven body, and even shortens the life of the oven body. In particular, if the carbon adhered to and grown on the oven wall surface is peeled off, level differences due to the irregularity formed on the oven wall surface often increase and therefore, the clogging in the oven becomes easier to occur upon the coke extrusion. Accordingly, it is very important for operating a coke oven to maintain smoothness of a wall surface in the coke oven.

However, in the operations presently performed, irregularity formed on oven wall surfaces in coke ovens is inevitable. Therefore, in order to prolong the life of an oven body as much as possible, it is necessary to ascertain the irregularity formed on the oven wall surface and appropriately perform repair to efficiently smooth out the irregularity.

As an oven wall shape measuring apparatus therefor, for example, a technique of capturing an oven wall surface images with a linear image camera and measuring irregular shapes using spot-like laser light is known (see Patent Literature 1). Moreover, a technique of performing, with a same imaging device, measurement of irregular shapes by irradiating slit-like laser light to an oven wall surface and imaging self-emitting light from the oven wall surface (e.g., light in the red spectrum region emitted from the red-hot oven wall surface) is also known (see Patent Literature 2).

CITATION LIST

Patent Literature

Patent Literature 1: Japanese Patent Application Laid-open 2000-266475
Patent Literature 2: Japanese Patent Application Laid-open 2004-77019

SUMMARY

Technical Problem

However, in the technique described in Patent Literature 1, the irregularity information on the oven wall is obtained by irradiating the spot-like laser light to one point of each oven wall brick and therefore, irregularity information is not able to be obtained for the entire surface of the oven wall. Moreover, in the technique described in Patent Literature 2, because the irradiation angle of the slit-like laser light is shallow, it is impossible to increase the measurable range in a direction perpendicular to the oven wall surface, and further, the laser light and the self-emitting light relating to the irregularity information are obtained simultaneously by the single imaging device and there is a problem that it is difficult to adjust both the incident brightness level of the laser light and that of the self-emitting light so as to prevent halation. Therefore, there has been a demand for an oven wall shape measuring apparatus in which laser light and self-emitting light for measuring an irregular shape of an oven wall surface do not interfere with each other and in which a measurable range in the direction perpendicular to the oven wall surface and an irradiation range of the laser light are wide.

The present invention has been made in view of the above and has an object to provide an oven wall shape measuring apparatus, an oven wall shape measuring system, and an oven wall shape measuring method, in which laser light and self-emitting light of an oven wall (i.e., light which is emitted from the oven wall due to the high temperature of the oven wall) for measuring an irregular shape of an oven wall surface are simultaneously obtained while allowing the laser light and the self-emitting light to not interfere with each other and a measurable range in a direction perpendicular to the oven wall surface and an irradiation range of the laser light to be wide.

Solution to Problem

An oven wall shape measuring apparatus according to the present invention includes: a slit laser light source that is arranged in a thermally-insulated protection box having a slit-like window and emits slit-like laser light; a laser light mirror that reflects the laser light and irradiates an oven wall surface with the laser light via the window; an imaging mirror that reflects reflected light due to irradiation of the laser light and self-emitting light emitted from the oven wall surface, the reflected light and the self-emitting light entering the thermally-insulated protection box via the window; and an imaging device that images, via an optical filter, the self-emitting light and the reflected light that are reflected from the imaging mirror.

An oven wall shape measuring system according to the present invention includes: the oven wall shape measuring apparatus according to the present invention; a position detecting unit that detects an intra-oven position of the oven wall shape measuring apparatus; and an image processing unit that generates a self-emitting light image of the oven wall surface and an image of an irregular shape from an image captured by the imaging device of the oven wall shape measuring apparatus and a position of the oven wall shape measuring apparatus.

An oven wall shape measuring system according to the present invention includes: an oven wall shape measuring apparatus that is capable of separately imaging, within one image, reflected light of slit-like laser light irradiated to an oven wall surface and self-emitting light emitted from the oven wall surface; a position detecting unit that detects an intra-oven position of the oven wall shape measuring apparatus; and an image processing unit that generates self-emitting light image of the oven wall surface and an image of an irregular shape, from an image captured by an imaging device of the oven wall shape measuring apparatus and an intra-oven position of the oven wall shape measuring apparatus.

An oven wall shape measuring method according to the present invention includes: a position detecting step, by a position detecting unit, of detecting an intra-oven position of an oven wall shape measuring apparatus; an imaging step, by the oven wall shape measuring apparatus, of separately imaging, within one image, reflected light of slit-like laser light irradiated to an oven wall surface and self-emitting light emitted from the oven wall surface; a one-dimensional self-emitting light line extracting step, by an image processing unit, of extracting a one-dimensional self-emitting light line of one line in a vertical direction in an image region of which the self-emitting light has been imaged; an irregular shape calculating step, by the image processing unit, of calculating a one-dimensional irregular shape line in a vertical direction of an oven wall based on a principle of triangulation from an image of the slit-like laser light in an image region of which the reflected light has been imaged; and an image generating step, by the image processing unit, of generating a self-emitting light image of the oven wall surface and an image of an irregular shape by using the intra-oven position of the oven wall shape measuring apparatus detected in the position detecting step, the one-dimensional self-emitting light line extracted in the one-dimensional self-emitting light line extracting step, and the one-dimensional irregular shape line extracted in the irregular shape calculating step.

ADVANTAGEOUS EFFECTS OF INVENTION

According to the oven wall shape measuring apparatus, the oven wall shape measuring system, and the oven wall shape measuring method according to the present invention, it is possible to simultaneously obtain the laser light and the self-emitting light of the oven wall for measuring the irregular shape of the oven wall surface while allowing the laser light and the self-emitting light to not interfere with each other and the measurable range in a direction perpendicular to the oven wall surface and the irradiation range of the laser light to be increased.

DESCRIPTION OF EMBODIMENTS

An embodiment of the present invention will be described below in detail with reference to drawings. The present invention is not limited to the present embodiment.

Figure 1:
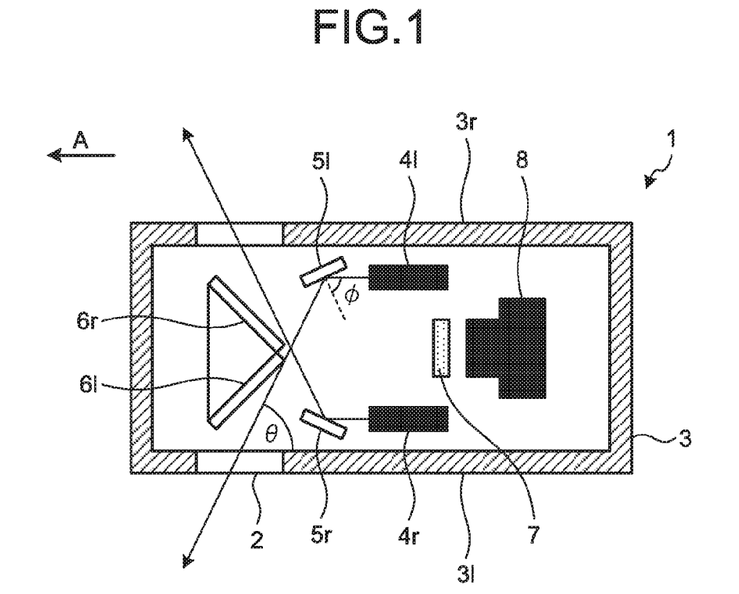
FIG. 1 is a schematic configuration diagram of an oven wall shape measuring apparatus according to an embodiment of the present invention.

FIG. 1 is a schematic configuration diagram of an oven wall shape measuring apparatus 1 according to the embodiment of the present invention. As illustrated in FIG. 1, the oven wall shape measuring apparatus 1 includes a slit laser light source 4 that is arranged in a thermally-insulated protection box 3 that has a slit-like window 2 and emits slit-like laser light, a laser light mirror 5 that reflects the laser light and directs the laser light to the oven wall surface via the window 2, an imaging mirror 6 that reflects the self-emitting light emitted from the oven wall surface and the reflected light from the oven wall surface due to the laser light, and an imaging device 8 that images via an optical filter 7 the self-emitting light and the reflected light reflected from the imaging mirror 6.

The oven wall shape measuring apparatus 1 in the present embodiment is configured to be capable of measuring the shape of the oven wall on the right side and the shape of the oven wall on the left side at the same time, and the slit laser light source 4, the laser light mirror 5, and the imaging mirror 6 include a pair of a right-oven-wall slit laser light source $4_r$ and a left-oven-wall slit laser light source $4_l$, a pair of a right-oven-wall laser light mirror $5_r$ and a left-oven-wall laser light mirror $5_l$, and a pair of a right-oven-wall imaging mirror $6_r$ and a left-oven-wall imaging mirror $6_l$, respectively. The optical filter 7 and the imaging device 8 are configured such that they are used both for measuring the shape of the oven wall on the right side and measuring the shape of the oven wall on the left side. In the following, components relating to measurement of the shape of the oven wall on the right side and components relating to measurement of the shape of the oven wall on the left side are distinguished by the indexes "r" and "l" added to the reference numbers. If it is not particularly necessary to distinguish between them, reference numbers without indexes are used. Moreover, the right side and the left side in the explanation are defined with reference to the direction of arrow A in the drawings.

The slit laser light source 4 in the oven wall shape measuring apparatus 1 in the present embodiment is arranged parallel to the longitudinal surface of the thermally-insulated protection box 3 and emits laser light such that the cross section of the slit-like laser light is parallel to the longitudinal surface of the thermally-insulated protection box 3. The laser light mirror 5 is arranged at an angle equal to or greater than 30° relative to the longitudinal surface of the thermally-insulated protection box 3 and is arranged such that the incident angle φ of the laser light is equal to or less than 60°.

At this time, the right-oven-wall slit laser light source $4_r$ for measuring the shape of the oven wall on the right side is arranged near a longitudinal surface $3_l$ on the left side of the longitudinal surface of the thermally-insulated protection box 3 and the left-oven-wall slit laser light source $4_l$ for measuring the shape of the oven wall on the left side is arranged near a longitudinal surface $3_r$ on the right side of the longitudinal surface of the thermally-insulated protection box 3. Specifically, the laser light emitted from the right-oven-wall slit laser light source $4_r$ and the laser light emitted from the left-oven-wall slit laser light source $4_l$ are reflected by the right-oven-wall laser light mirror $5_r$ and the left-oven-wall laser light mirror $5_l$, respectively, and irradiate the oven wall such that the optical paths thereof intersect each other.

With the above configuration, the oven wall shape measuring apparatus 1 in the present embodiment can effectively extend the length of the optical path of the laser light even though the thermally-insulated protection box 3 is small. The volume to be cooled can be suppressed by reducing the size of the thermally-insulated protection box 3 and, moreover, the measurable range in the height direction of the coke oven by one oven wall shape measuring apparatus 1 can be kept large by extending the length of the optical path. Therefore, when a plurality of the oven wall shape measuring apparatuses 1 are arranged in the height direction and are used for measurement of the entire coke oven, the number of apparatuses can be suppressed. For example, the shortest distance between the wall surfaces in the coke oven that uses the oven wall shape measuring apparatus 1 according to the present embodiment of the present invention is about 300 mm. Thus, the width of the oven wall shape measuring apparatus 1 (i.e., the width of the thermally-insulated protection box 3) needs to be made smaller than 300 mm described above. For example, in the oven wall shape measuring apparatus 1 in the present embodiment of the present invention, even if the thermally-insulated protection box 3 is designed to have a width of 250 mm and a length of 500 mm in the longitudinal direction, it is possible to effectively use the distance obliquely across the thermally-insulated protection box 3. Therefore, the length of the optical path of the laser light can be set at about 250 to 500 mm. At this time, if the slit laser light source 4 that has a divergence angle of 90° is used, the irradiation range of the laser light in the line direction (slit direction) can be kept as wide as about 500 to 1000 mm.

The imaging device 8 in the oven wall shape measuring apparatus 1 in the present embodiment captures images of the oven wall on the right side and the oven wall on the left side at the same time via reflections from the right-oven-wall imaging mirror $6_r$ and the left-oven-wall imaging mirror $6_l$. At this time, as will be described later, the self-emitting light emitted from the oven wall surface and the reflected light from the oven wall surface due to the laser light are separated by the optical filter 7 and are imaged. In other words, the imaging device 8 obtains the self-emitting light and the reflected light of the laser light from the right side oven wall and the self-emitting light and the reflected light of the laser light from the left side oven wall at the same time.

The right-oven-wall imaging mirror $6_r$ and the left-oven-wall imaging mirror $6_l$ are arranged at an angle substantially 90° to each other so that the oven wall on the right side and the oven wall on the left side can be appropriately imaged via the right-oven-wall imaging window 2 and the left-oven-wall imaging window 2, which are provided at bilaterally symmetrical positions in the thermally-insulated protection box 3.

Next, a field of view F and a measurable range R of the oven wall shape measuring apparatus 1 according to the present embodiment will be described with reference to FIG. 2.

Figure 2:
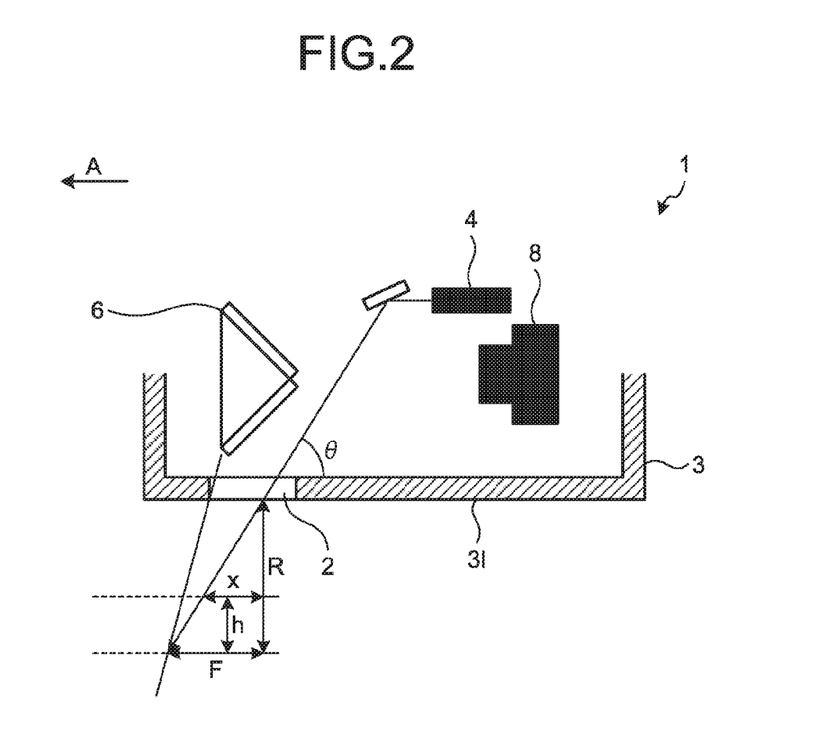
FIG. 2 is a partial configuration diagram of the oven wall shape measuring apparatus according to the embodiment of the present invention.

FIG. 2 is a partial configuration diagram illustrating only the configuration relating to measurement of the left-side oven wall in the oven wall shape measuring apparatus 1. The configuration relating to measurement of the right-side oven wall is omitted because the oven wall shape measuring apparatus 1 according to the present embodiment has a symmetrical configuration. As illustrated in FIG. 2, the laser light emitted from the slit laser light source 4 irradiates part of the field of view F of the imaging device 8. At this time, the laser light emitted from the slit laser light source 4 irradiates the oven wall at the irradiation angle θ (in this embodiment, the angle between the laser light and the longitudinal surface of the thermally-insulated protection box 3); therefore, if there are irregularities on the oven wall in the field of view F, the irradiation position of the laser light changes. FIG. 2 indicates that, if there is a protrusion with a height h in the field of view F, the irradiation position of the laser light changes to the position at the distance x from the end of the field of view.

On the basis of the above observation, it can be seen that the measureable range R of the oven wall shape measuring apparatus 1 according to the present embodiment of the present invention is determined on the basis of the field of view F and the irradiation angle θ and the following relationship is satisfied.

$$\text{Measureable range } R = \text{Field of view } F \times \tan \theta \qquad (1)$$

Therefore, a preferable size or configuration for the oven wall shape measuring apparatus 1 according to the present embodiment of the present invention is derived as follows.

The shortest distance between the wall surfaces in the coke oven that uses the oven wall shape measuring apparatus 1 according to the present embodiment of the present invention is about 300 mm. Thus, the width of the oven wall shape measuring apparatus 1, i.e., the width of the thermally-insulated protection box 3, needs to be made less than 300 mm described above. Therefore, the width of the imaging mirror 6 on each of the right and left sides needs to be within 150 mm. Furthermore, the thickness of the thermally-insulated protection box 3 and the size of the space for a jig such as a casing for attaching the imaging mirror 6 need to be included in the width of 150 mm. Thus, the imaging mirror 6 has a width of within about 100 mm. Consequently, even if the spread due to the angle of view of the imaging device 8 is taken into consideration, the field of view F of the imaging device 8 becomes a maximum of about 120 mm.

On the other hand, the maximum distance between the wall surfaces in the coke oven is about 450 mm. Moreover, if it is considered that the range of irregularities due to deterioration of bricks is about 50 mm, the required measurable range R is obtained as follows: oven-wall-surface maximum width (450 mm)−apparatus width (about 300 mm)+irregularity range (about 50 mm)=200 mm. When the relationship of Equation (1) is considered, because 120 mm×tan)(60°)≈200 mm, it is derived that the irradiation angle θ needs to be equal to or greater than 60° in the oven wall shape measuring apparatus 1 according to the present embodiment of the present invention.

The incident angle φ of the laser light and the irradiation angle θ have the relationship of 180°=2φ+θ. On the basis of this relationship, the condition that the irradiation angle is equal to or greater than 60° is satisfied by arranging the laser light mirror 5 at an angle equal to or greater than 30° relative to the longitudinal surface of the thermally-insulated protection box 3 and by setting the incident angle φ to be equal to or less than 60°.

Next, the operational effect of the optical filter 7 in the oven wall shape measuring apparatus 1 according to the present embodiment will be described with reference to FIG. 3 and FIG. 4.

Figure 3:
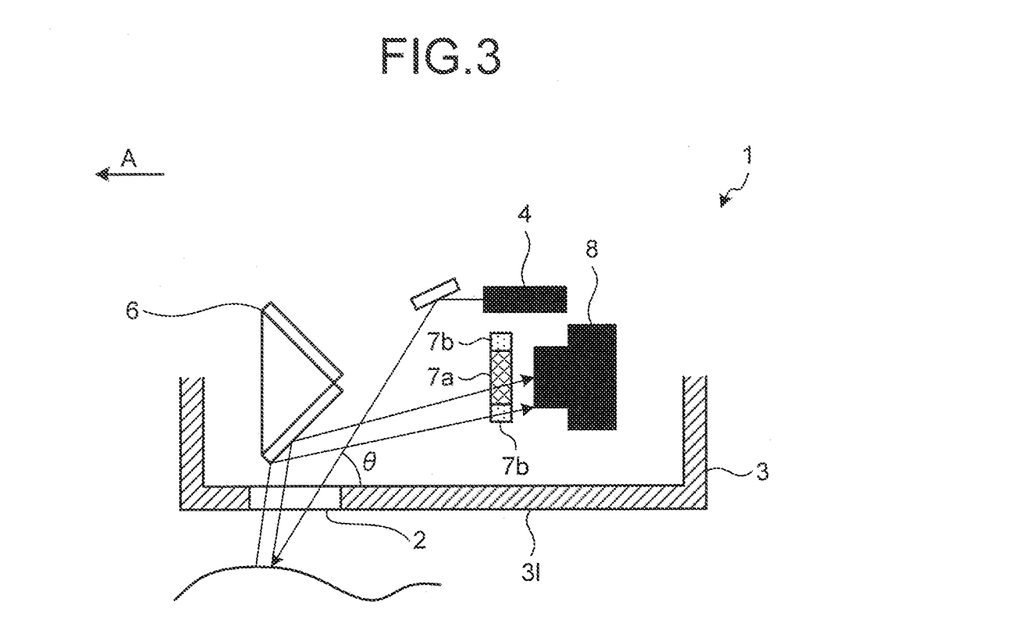
FIG. 3 is a diagram illustrating optical paths of the self-emitting light and the reflected light.

FIG. 3 is a diagram illustrating optical paths of the self-emitting light emitted from the oven wall surface and the reflected light from the oven wall surface due to the laser light when the imaging device 8 images the oven wall surface. As illustrated in FIG. 3, the self-emitting light emitted from the oven wall surface and the reflected light from the oven wall surface due to the laser light are the same in that they enter the thermally-insulated protection box 3 through the window 2 provided in the thermally-insulated protection box 3 and are reflected from the imaging mirror 6, and, thereafter, are transmitted through the optical filter 7 and enter the imaging device 8. However, the self-emitting light and the reflected light are transmitted through different regions of the optical filter 7. In the example illustrated in FIG. 3, the reflected light is transmitted through a reflected light transmission region 7a of the optical filter 7 and the self-emitting light is transmitted through a self-emitting light transmission region 7b of the optical filter 7.

Figure 4:
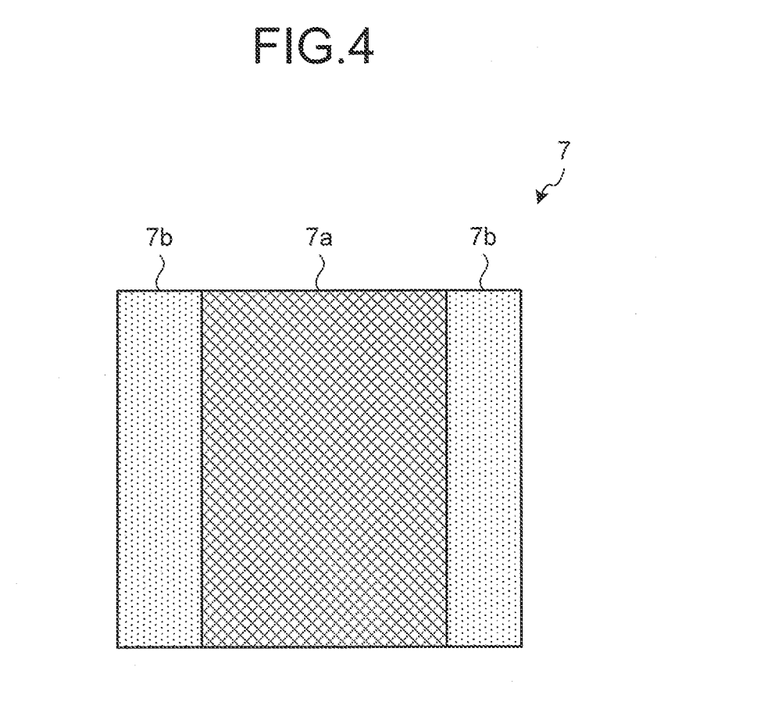
FIG. 4 is a schematic diagram of an enlarged optical filter.

FIG. 4 is a schematic diagram of the enlarged optical filter 7. In FIG. 4, the reflected light transmission region 7a is a band-like region in the middle of the optical filter 7 and the self-emitting light transmission regions 7b are band-like regions that border both sides of the reflected light transmission region 7a. The reflected light transmission region 7a is a narrow bandpass filter through which the laser light wavelength of the slit laser light source 4 is transmitted and the self-emitting light transmission region 7b is a wide bandpass filter through which the self-emitting light from the oven wall is transmitted. Therefore, the band-like region of the reflected light transmission region 7a in the optical filter 7 is configured as a band-like region parallel to the slit direction, i.e., in a direction same as the vertical direction of the oven wall, so that the reflected light from the oven wall surface due to the laser light from the slit laser light source 4 is able to be transmitted therethrough. Moreover, the band-like regions of the self-emitting light transmission regions 7b in the optical filter 7 are band-like regions that border both sides of the reflected light transmission region 7a and are therefore necessarily configured as band-like regions parallel to the slit direction.

For the oven wall shape measuring apparatus 1 according to the present embodiment of the present invention to image the irradiation position of the laser light by the imaging device 8, it is necessary to satisfy condition A, which is that the brightness of the reflected light due to the laser light is larger than the brightness of the self-emitting light from the oven wall. However, if the optical filter 7 having a single wavelength characteristic is used for the oven wall shape measuring apparatus 1, it is difficult to adjust the output of the slit laser light source 4 so as to satisfy condition A. Therefore, in the oven wall shape measuring apparatus 1 according to the present embodiment of the present invention, regions with different wavelength characteristics are generated in the optical filter 7; therefore, the brightness of the reflected light due to the laser light is controlled so as to be always larger than the brightness of the self-emitting light from the oven wall in the range in which the laser light is imaged.

Next, an oven wall shape measuring method according to the present embodiment of the present invention explained above will be described. In the following, an explanation of the oven wall shape measuring method will be given in accordance with an oven wall shape measuring system in which the oven wall shape measuring apparatus 1 according to the present embodiment of the present invention is used; however, the oven wall shape measuring method according to the present embodiment of the present invention is not necessarily performed by using the oven wall shape measuring system in which the oven wall shape measuring apparatus 1 is used.

Figure 5:
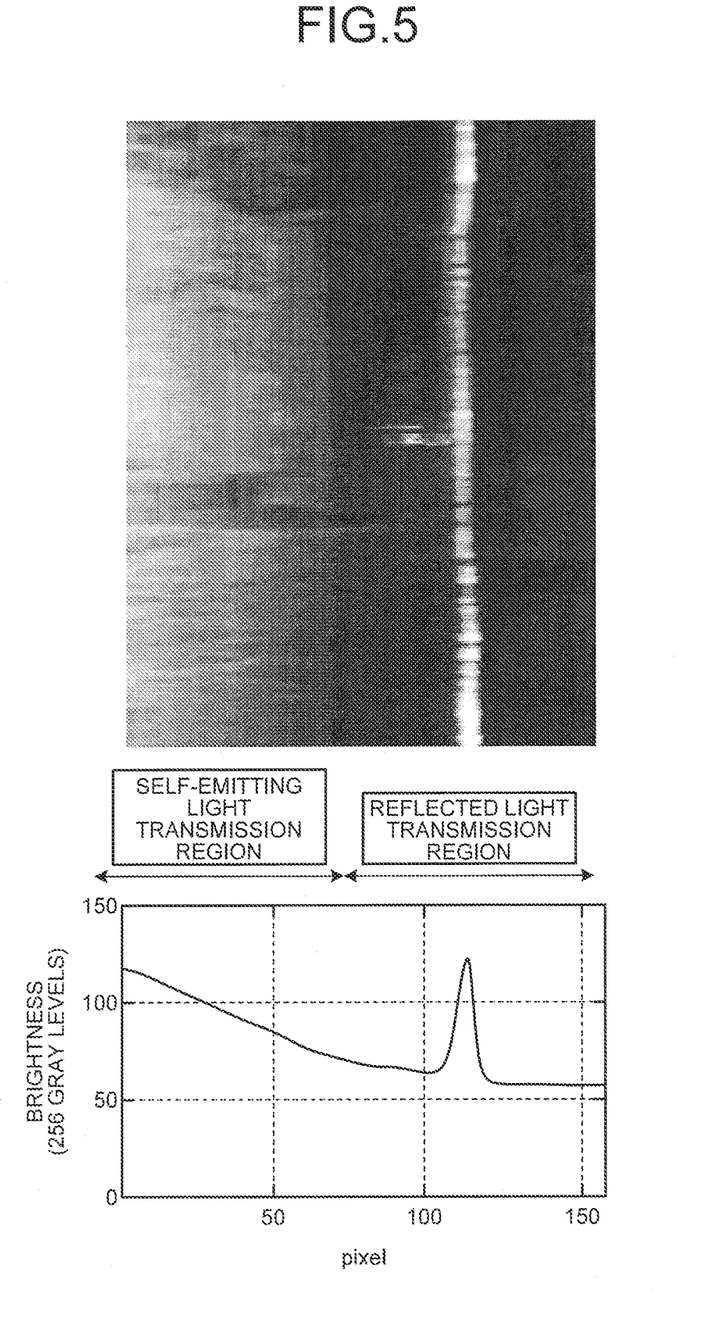
FIG. 5 is a graph of an image captured by an imaging device and its brightness distribution.

FIG. 5 illustrates in a comparative manner part of an image inside the coke oven captured by the imaging device 8 and a graph obtained by averaging and quantifying the brightness distribution of the part of the image in the vertical direction along the lateral direction. The image in the upper part in FIG. 5 is an image obtained by cutting out the left half of the image corresponding to the left-side oven wall from one image inside the coke oven captured by the imaging device 8 and thereafter cutting out part thereof in the longitudinal direction, and is a region in which the self-emitting light emitted from the left-side oven wall surface and the slit-like laser light reflected from the left-side oven wall are included. The brightness of the image illustrated in FIG. 5 is obtained with 256 gray levels and the values (i.e., longitudinal axis) in the graph obtained by averaging and quantifying the brightness in the vertical direction of the image also has 256 gray levels.

A portion near the left end of the image in the upper part in FIG. 5 (the positions between 0 and 50 pixels in the lateral direction) and the remaining region (the positions between 50 and 150 pixels in the lateral direction) are obtained by imaging light beams obtained via the self-emitting light transmission region 7b of the optical filter 7 and the reflected light transmission region 7a of the optical filter 7, respectively. In the following, an image of the light beam obtained via the reflected light transmission region 7a of the optical filter 7 is referred to as a reflected light image and an image of the light beam obtained via the self-emitting light transmission region 7b is referred to as a self-emitting light image. Moreover, a region corresponding to the reflected light image in the image in the upper part in FIG. 5 is referred to as a reflected light image region and a region corresponding to the self-emitting light image is referred to as a self-emitting light image region.

As is seen from the image in the upper part and the graph in the lower part in FIG. 5, although the peak brightness of the laser light and the brightness of the self-emitting light are the same level in the self-emitting light image region near the left side, the brightness of the reflected light due to the laser light becomes greater than the brightness of the self-emitting light from the oven wall in the reflected light image region on the right side. Therefore, according to the oven wall shape measuring apparatus 1 in the present embodiment of the present invention, because the optical filter 7 includes the reflected light transmission region 7a and the self-emitting light transmission region 7b, the reflected light due to the laser light and the self-emitting light from the oven wall do not mutually cause halation and the reflected light and the self-emitting light can be obtained at the same time. In the following, the procedure for combining the self-emitting light image and the shape image of the oven wall from an image represented by FIG. 5 will be described with reference to the flowchart in FIG. 6.

Figure 6:
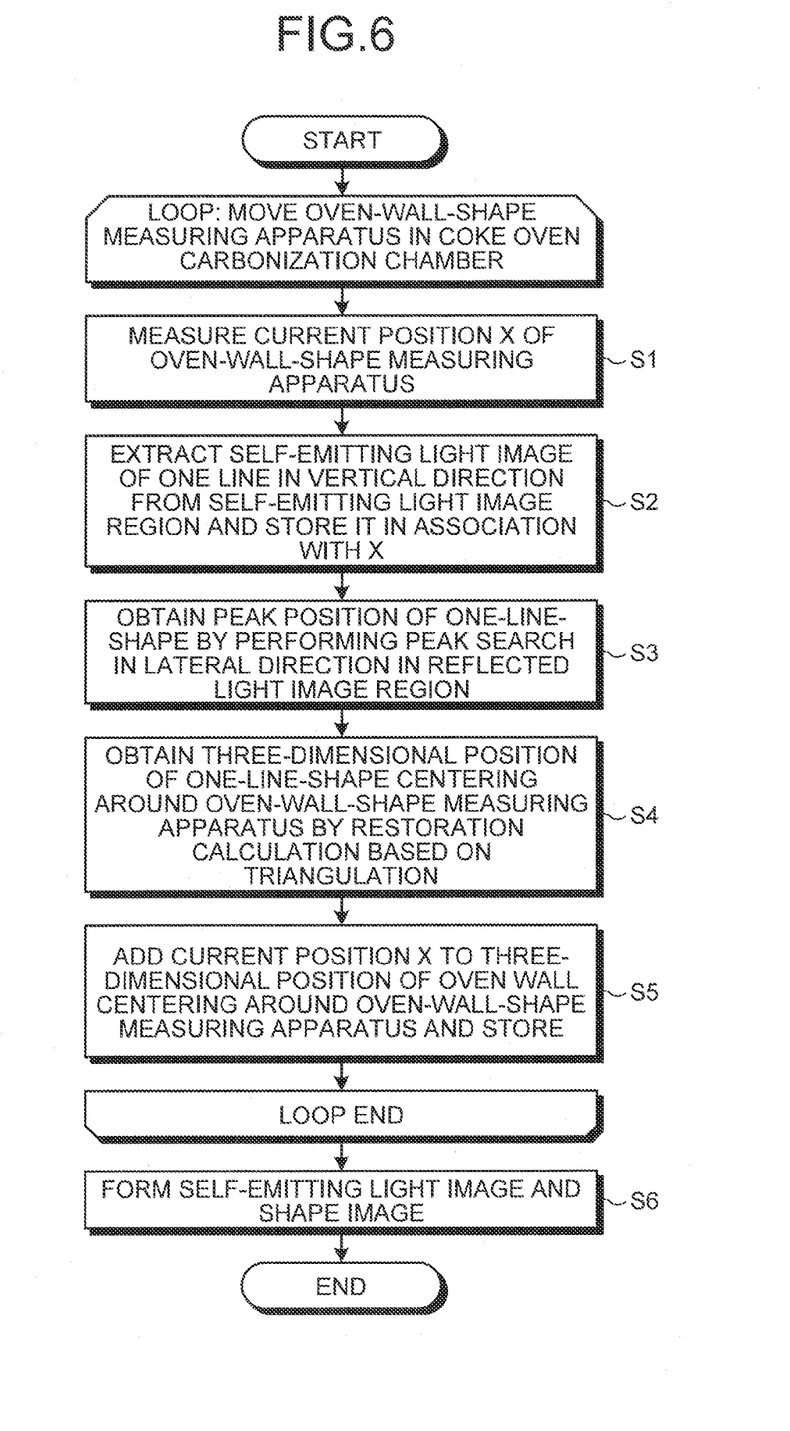
FIG. 6 is a flowchart illustrating a method of combining a self-emitting light image and a shape image of the oven wall that forms part of an oven wall shape measuring method according to the embodiment of the present invention.

FIG. 6 is a flowchart illustrating a method of combining the self-emitting light image and the shape image of the oven wall that forms part of the oven wall shape measuring method according to the embodiment of the present invention.

As illustrated in FIG. 6, the method of combining the self-emitting light image and the shape image of the oven wall is composed of performing a loop of the following process at each position by moving the oven wall shape measuring apparatus 1 in the coke oven carbonization chamber. When the current position X of the oven wall shape measuring apparatus 1 in the coke oven carbonization chamber is measured, the above-described loop starts (Step S1). At this time, the current position X of the oven wall shape measuring apparatus 1 is measured by a position detecting unit that detects the position of the oven wall shape measuring apparatus 1 and is additionally provided in the oven wall shape measuring system in which the oven wall shape measuring apparatus 1 is used.

The position detecting unit that detects the position of the oven wall shape measuring apparatus 1 can be realized by a method for measuring the rotation of a drive motor that drives the oven wall shape measuring apparatus 1 by a PLG or the like, a method in which a laser rangefinder using a time-of-flight method is used, or the like.

Next, one line in the vertical direction near the left end in the self-emitting light image region is extracted as a self-emitting light part at the time of imaging and is stored in a storing unit in association with the current position X of the oven wall shape measuring apparatus 1 (Step S2). The storing unit in Step S2 can be realized by a memory included in an image processing unit of the oven wall shape measuring system. One vertical line in the self-emitting light image region, i.e., one line in the vertical direction of the oven wall, can be arbitrarily selected within a range in which halation does not occur and the self-emitting light has an appropriate intensity.

Next, the peak of the brightness is searched for in each line in the lateral direction in the reflected light image region so as to obtain the peak position data of one line (Step S3). The peak position of the laser light obtained by performing the process in Step S3 is determined on the basis of the positional relationship between the imaging device and the laser light, and the peak position can be converted to a three-dimensional position centering around the oven wall shape measuring apparatus 1 by using a typical reconstruction calculation on the basis of the principle of triangulation (see FIG. 2) (Step S4).

The current position X of the oven wall shape measuring apparatus 1 is added to the three-dimensional position of the one-line-shape obtained by the above process, which is stored as three-dimensional data on the oven wall shape corresponding to the position in the oven length direction in the coke oven carbonization chamber, i.e., the horizontal direction (Step S5).

Figure 7:
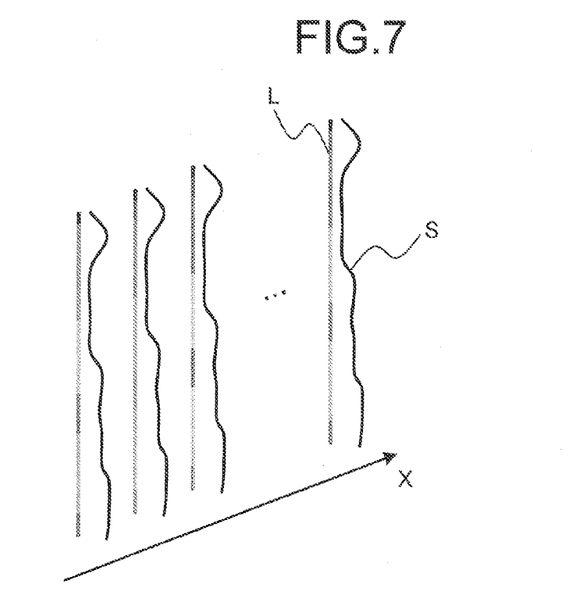
FIG. 7 is a diagram schematically representing one-line data of the self-emitting light and the shape of the oven wall obtained for each current position X of an oven wall shape measuring apparatus 1.

The above process is repeated while advancing or retracting the oven wall shape measuring apparatus 1 by performing the loop of Steps S1 to S5, whereby it is possible to obtain one-line data in the vertical direction for the self-emitting light and the shape of the oven wall corresponding to each current position X of the oven wall shape measuring apparatus 1. FIG. 7 is a diagram schematically representing one-line data of the self-emitting light and the shape of the oven wall obtained for each current position X of the oven wall shape measuring apparatus 1.

In this manner, the self-emitting light image and the shape image of the oven wall can be formed by arranging one-line data of the self-emitting light and the shape of the oven wall, which is obtained for each current position X of the oven wall shape measuring apparatus 1, with respect to the current position X of the oven wall shape measuring apparatus 1 (Step S6). Because the coke oven carbonization chamber has a certain height, all the self-emitting light images and the shape images of the oven wall in a height direction of the oven can be obtained by arranging oven wall shape measuring apparatuses 1 in the height direction and performing the measurement.

Figure 8:
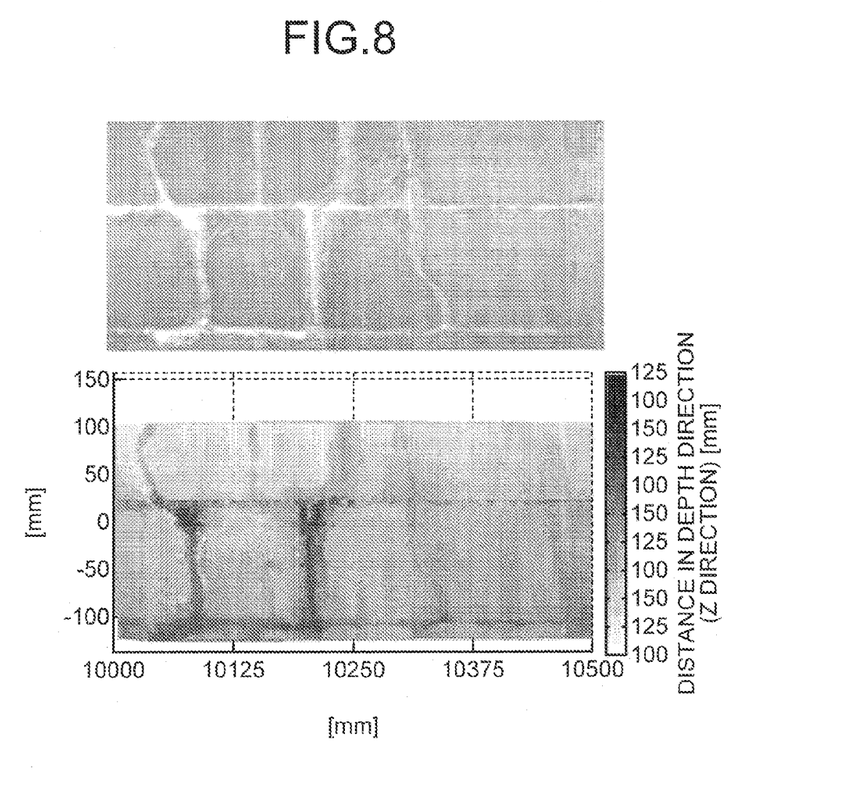
FIG. 8 is a self-emitting light image of the oven wall bricks and an image of the irregular shape.

FIG. 8 illustrates an image displaying the self-emitting light image of the oven wall bricks and the irregular shape of the oven wall imaged by using the oven wall shape measuring apparatus 1 according to the present embodiment of the present invention in grayscale. In FIG. 8, in the self-emitting light image in the upper section, the brightness of the self-emitting light of the oven wall bricks is displayed in grayscale, and in the image illustrating the irregular shape of the oven wall in the lower section, the distance in the depth direction is displayed in grayscale. The image illustrated in FIG. 8 can be generated from the image (for example, the image illustrated in FIG. 5) obtained by the imaging device 8 of the oven wall shape measuring apparatus 1 and from the intra-oven position of the oven wall shape measuring apparatus 1. Therefore, the oven wall shape measuring system in which the oven wall shape measuring apparatus 1 according to the present embodiment of the present invention is used additionally includes a unit that measures the intra-oven position of the oven wall shape measuring apparatus 1 and the image processing unit that generates the self-emitting light image of the oven wall surface and the image of the irregular shape from the image obtained by the imaging device 8. In FIG. 8, it can be seen that the oven wall shape measuring apparatus 1 according to the present embodiment of the present invention can obtain both the self-emitting light image and the irregular shape of the bricks at the same time.

As described above, the oven wall shape measuring apparatus 1 according to the present embodiment of the present invention includes the slit laser light source 4 that is arranged in the thermally-insulated protection box 3 that includes the slit-like window 2 and emits slit-like laser light, the laser light mirror 5 that reflects the laser light and irradiates an oven wall surface with the laser light via the window 2, the imaging mirror 6 that reflects reflected light from the oven wall surface due to irradiation of the laser light and self-emitting light emitted from the oven wall surface, which enter the thermally-insulated protection box 3 via the window 2, and the imaging device 8 that images via the optical filter 7 the self-emitting light and the reflected light that are reflected from the imaging mirror 6. Therefore, the irradiation angle of the laser light can be made deep and the length of the optical path of the laser light can be kept long. Consequently, the measurable range in the direction perpendicular to the oven wall surface and the irradiation range of the laser light can be increased without increasing the size of the oven wall shape measuring apparatus 1.

Moreover, in the oven wall shape measuring apparatus 1 according to the present embodiment of the present invention, the optical filter 7 includes the reflected light transmission region 7a that has a narrow bandpass characteristic of transmitting therethrough a wavelength of the laser light and the self-emitting light transmission region 7b that has a wide bandpass characteristic of transmitting therethrough a wavelength of the self-emitting light. Therefore, halation does not occur even if the irregular shape and the self-emitting light of the oven wall are measured at the same time.

Furthermore, the oven wall shape measuring system in which the oven wall shape measuring apparatus 1 according to the present embodiment of the present invention is used, includes a position detecting unit that detects a position of the oven wall shape measuring apparatus 1 and an image processing unit that generates a self-emitting light image of the oven wall surface and an image of an irregular shape from an image captured by the imaging device 8 of the oven wall shape measuring apparatus 1 and a position of the oven wall shape measuring apparatus 1. Therefore, the deterioration state of the oven can be recognized in a complex manner. While the deterioration state of the irregularity can be determined from the irregular shape image, the difference in thermal conduction for each brick and the surface state of the bricks can be determined from the self-emitting light image. The life of the oven can be prolonged by strategically repairing the oven on the basis of the above information.

Furthermore, in the oven wall shape measuring system in which the oven wall shape measuring apparatus 1 according to the present embodiment of the present invention is used, the image processing unit generates the self-emitting light image of the oven wall surface and the image of the irregular shape by sorting a one-dimensional self-emitting light line of one line in a vertical direction in an image region in which the self-emitting light is imaged and a one-dimensional irregular shape line obtained by calculating an irregular shape of one line in a vertical direction of an oven wall on a basis of principle of triangulation from an image of the slit-like laser light in an image region in which the reflected light is imaged, with respect to an intra-oven position of the oven wall shape measuring apparatus 1 detected by the position detecting unit. Therefore, both the self-emitting light image and the irregular shape of the bricks of the oven wall can be obtained at the same time.

Moreover, the oven wall shape measuring system according to the present embodiment of the present invention includes the oven wall shape measuring apparatus 1 that is capable of separately imaging reflected light of slit-like laser light emitted to an oven wall surface and self-emitting light emitted from the oven wall surface in one image, a position detecting unit that detects an intra-oven position of the oven wall shape measuring apparatus 1, and an image processing unit that generates a self-emitting light image of the oven wall surface and an image of an irregular shape from an image captured by the imaging device 8 of the oven wall shape measuring apparatus 1 and an intra-oven position of the oven wall shape measuring apparatus 1. Therefore, the deterioration state of the oven can be recognized in a complex manner. While the deterioration state of the irregularity can be determined from the irregular shape image, the difference in thermal conduction for each brick and the surface state of the bricks can be determined from the self-emitting light image. The life of the oven can be prolonged by strategically repairing the oven on the basis of the above information.

Furthermore, in the oven wall shape measuring system according to the present embodiment of the present invention, the image processing unit generates the self-emitting light image of the oven wall surface and the image of the irregular shape by sorting a one-dimensional self-emitting light line of one line in a vertical direction in an image region in which the self-emitting light is imaged and a one-dimensional irregular shape line obtained by calculating an irregular shape of one line in a vertical direction of an oven wall on a basis of a principle of triangulation from an image of the slit-like laser light in an image region in which the reflected light is imaged, with respect to an intra-oven position of the oven wall shape measuring apparatus 1 detected by the position detecting unit. Therefore, both the self-emitting light image and the irregular shape of the bricks of the oven wall can be obtained at the same time.

Moreover, the oven wall shape measuring method according to the present embodiment of the present invention includes a position detecting step of detecting an intra-oven position of the oven wall shape measuring apparatus 1 by a position detecting unit, an imaging step of separately imaging reflected light of slit-like laser light emitted to an oven wall surface and self-emitting light emitted from the oven wall surface in one image, by the oven wall shape measuring apparatus 1, a one-dimensional self-emitting light line extracting step of extracting a one-dimensional self-emitting light line of one line in a vertical direction in an image region in which the self-emitting light is imaged, by an image processing unit, an irregular shape calculating step of calculating a one-dimensional irregular shape line in a vertical direction of an oven wall on a basis of a principle of triangulation from an image of the slit-like laser light in an image region in which the reflected light is imaged, by the image processing unit, and an image generating step of generating a self-emitting light image of the oven wall surface and an image of an irregular shape by the image processing unit using the intra-oven position of the oven wall shape measuring apparatus detected in the position detecting step, the one-dimensional self-emitting light line extracted in the one-dimensional self-emitting light line extracting step, and the one-dimensional irregular shape line extracted in the irregular shape calculating step. Therefore, the deterioration state of the oven can be recognized in a complex manner. While the deterioration state of the irregularity can be determined from the irregular shape image, the difference in thermal conduction for each brick and the surface state of the bricks can be determined from the self-emitting light image. The life of the oven can be prolonged by strategically repairing the oven on the basis of the above information.

Furthermore, in the oven wall shape measuring method according to the present embodiment of the present invention, the image generating step includes generating the self-emitting light image of the oven wall surface and the image of the irregular shape by sorting the one-dimensional self-emitting light line extracted in the one-dimensional self-emitting light line extracting step and the one-dimensional irregular shape line extracted in the irregular shape calculating step with respect to an intra-oven position of the oven wall shape measuring apparatus 1 by the image processing unit. Therefore, both the self-emitting light image and the irregular shape of the bricks of the oven wall can be obtained at the same time.

REFERENCE SIGNS LIST

1 oven wall shape measuring apparatus
2 window
3 thermally-insulated protection box
4 slit laser light source
5 laser light mirror
6 imaging mirror
7 optical filter
8 imaging device

The invention claimed is:

1. An oven wall shape measuring apparatus, comprising:
   a slit laser light source that is arranged in a thermally-insulated protection box having a slit-like window and emits slit-like laser light;
   a laser light mirror that reflects the laser light and irradiates an oven wall surface with the laser light via the window;
   an imaging mirror that reflects reflected light due to irradiation of the laser light and self-emitting light emitted from the oven wall surface, the reflected light and the self-emitting light entering the thermally-insulated protection box via the window, wherein the self-emitting light is light which is emitted from the oven wall surface due to high temperature of the oven wall surface;
   an optical filter that has a first transmission region having bandpass characteristics of a narrow band and transmitting there through a wavelength of the laser light, and a second transmission region having bandpass characteristics of a broad band and transmitting therethrough a wavelength of the self-emitting light, the first transmission region and the second transmission region being arranged in parallel to each other in an incidence plane of the optical filter; and
an imaging device that images, via the optical filter, the self-emitting light and the reflected light that are reflected from the imaging mirror.

2. The oven wall shape measuring apparatus according to claim 1, wherein:
an optical axis of the laser light emitted from the slit laser light source is arranged parallel to a longitudinal surface of the thermally-insulated protection box, and
an incident angle of the laser light relative to the laser light mirror is equal to or less than 60 degrees.

3. An oven wall shape measuring system, comprising:
the oven wall shape measuring apparatus according to claim 1;
a position detecting unit that detects an intra-oven position of the oven wall shape measuring apparatus; and
an image processing unit that generates a self-emitting light image of the oven wall surface and an image of an irregular shape from an image captured by the imaging device of the oven wall shape measuring apparatus and a position of the oven wall shape measuring apparatus.

4. The oven wall shape measuring system according to claim 3, wherein the image processing unit generates the self-emitting light image of the oven wall surface and the image of the irregular shape by sorting, with respect to an intra-oven position of the oven wall shape measuring apparatus detected by the position detecting unit:
a one-dimensional self-emitting light line of one line in a vertical direction in an image region of which the self-emitting light has been imaged; and
a one-dimensional irregular shape line obtained by calculating an irregular shape of one line in a vertical direction of an oven wall based on a principle of triangulation from an image of the slit-like laser light in an image region of which the reflected light has been imaged.

5. An oven wall shape measuring system, comprising:
an oven wall shape measuring apparatus that is capable of separately imaging, within one image, reflected light of slit-like laser light irradiated to an oven wall surface and self-emitting light emitted from the oven wall surface by use of an optical filter that has a first transmission region having bandpass characteristics of a narrow band and transmitting there through a wavelength of the laser light, and a second transmission region having bandpass characteristics of a broad band and transmitting therethrough a wavelength of the self-emitting light, the first transmission region and the second transmission region being arranged in parallel to each other in an incidence plane of the optical filter, wherein the self-emitting light is light which is emitted from the oven wall surface due to high temperature of the oven wall surface;
a position detecting unit that detects an intra-oven position of the oven wall shape measuring apparatus; and
an image processing unit that generates a self-emitting light image of the oven wall surface and an image of an irregular shape, from an image captured by an imaging device of the oven wall shape measuring apparatus and an intra-oven position of the oven wall shape measuring apparatus.

6. The oven wall shape measuring system according to claim 5, wherein the image processing unit generates the self-emitting light image of the oven wall surface and the image of the irregular shape by sorting, with respect to an intra-oven position of the oven wall shape measuring apparatus detected by the position detecting unit:
a one-dimensional self-emitting light line of one line in a vertical direction in an image region of which the self-emitting light has been imaged and a one-dimensional irregular shape line obtained by calculating an irregular shape of one line in a vertical direction of an oven wall based on a principle of triangulation from an image of the slit-like laser light in an image region of which the reflected light has been imaged.

7. An oven wall shape measuring method for measuring an oven wall shape using an oven wall shape measuring apparatus which comprises a slit laser light source and an imaging device, the method comprising:
detecting an intra-oven position of the oven wall shape measuring apparatus;
separately imaging, within one image, reflected light of slit-like laser light irradiated to an oven wall surface and self-emitting light emitted from the oven wall surface, with the oven wall shape measuring apparatus, by use of an optical filter of the oven wall shape measuring apparatus, wherein the optical filter that has a first transmission region having bandpass characteristics of a narrow band and transmitting there through a wavelength of the laser light, and a second transmission region having bandpass characteristics of a broad band and transmitting therethrough a wavelength of the self-emitting light, the first transmission region and the second transmission region being arranged in parallel to each other in an incidence plane of the optical filter, and wherein the self-emitting light is light which is emitted from the oven wall surface due to high temperature of the oven wall surface;
extracting a one-dimensional self-emitting light line of one line in a vertical direction in an image region of which the self-emitting light has been imaged;
calculating a one-dimensional irregular shape line in a vertical direction of an oven wall based on a principle of triangulation from an image of the slit-like laser light in an image region of which the reflected light has been imaged; and
generating a self-emitting light image of the oven wall surface and an image of an irregular shape by using the detected intra-oven position of the oven wall shape measuring apparatus, the extracted one-dimensional self-emitting light line, and the calculated one-dimensional irregular shape line.

8. The oven wall shape measuring method according to claim 7, wherein the generating includes generating the self-emitting light image of the oven wall surface and the image of the irregular shape by sorting, with respect to an intra-oven position of the oven wall shape measuring apparatus:
the extracted one-dimensional self-emitting light line; and
the calculated one-dimensional irregular shape line.

9. An oven wall shape measuring system, comprising:
the oven wall shape measuring apparatus according to claim 2;
a position detecting unit that detects an intra-oven position of the oven wall shape measuring apparatus; and
an image processing unit that generates a self-emitting light image of the oven wall surface and an image of an irregular shape from an image captured by the imaging device of the oven wall shape measuring apparatus and a position of the oven wall shape measuring apparatus.

10. The oven wall shape measuring system according to claim 9, wherein the image processing unit generates the self-emitting light image of the oven wall surface and the image of the irregular shape by sorting, with respect to an intra-oven position of the oven wall shape measuring apparatus detected by the position detecting unit:
- a one-dimensional self-emitting light line of one line in a vertical direction in an image region of which the self-emitting light has been imaged; and
- a one-dimensional irregular shape line obtained by calculating an irregular shape of one line in a vertical direction of an oven wall based on a principle of triangulation from an image of the slit-like laser light in an image region of which the reflected light has been imaged.

* * * * *